(12) United States Patent
Takahashi et al.

(10) Patent No.: US 10,485,737 B2
(45) Date of Patent: Nov. 26, 2019

(54) DENTAL CURABLE COMPOSITION HAVING HIGH MECHANICAL STRENGTH

(71) Applicant: KABUSHIKI KAISHA SHOFU, Kyoto (JP)

(72) Inventors: Shuhei Takahashi, Kyoto (JP); Hidefumi Fujimura, Kyoto (JP); Jun Uchida, Kyoto (JP); Mitsuji Teramae, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 112 days.

(21) Appl. No.: 15/862,955

(22) Filed: Jan. 5, 2018

(65) Prior Publication Data
US 2018/0214352 A1    Aug. 2, 2018

(30) Foreign Application Priority Data

Jan. 31, 2017 (JP) ................................. 2017-015078

(51) Int. Cl.
*A61K 6/083*    (2006.01)
*A61K 6/00*    (2006.01)

(52) U.S. Cl.
CPC ............ *A61K 6/083* (2013.01); *A61K 6/0023* (2013.01); *A61K 6/0079* (2013.01); *A61K 6/0082* (2013.01); *A61K 6/0088* (2013.01); *A61K 6/0091* (2013.01); *A61K 6/0097* (2013.01)

(58) Field of Classification Search
CPC ...................................................... A61K 6/083
See application file for complete search history.

(56) References Cited

U.S. PATENT DOCUMENTS

| 5,320,886 | A | | 6/1994 | Bowen | |
|---|---|---|---|---|---|
| 5,749,733 | A | * | 5/1998 | Qian | ............ C09J 4/00 106/35 |
| 6,143,919 | A | * | 11/2000 | Shen | ............ C07C 271/16 560/158 |
| 7,619,016 | B2 | * | 11/2009 | Dickens | ............ A61K 6/0017 433/2 |
| 2003/0018098 | A1 | | 1/2003 | Falsafi et al. | |
| 2011/0275035 | A1 | * | 11/2011 | Lu | .......................... A61K 6/083 433/216 |
| 2012/0129973 | A1 | | 5/2012 | Sun | |

FOREIGN PATENT DOCUMENTS

| EP | 3 135 270 | | 3/2017 | |
|---|---|---|---|---|
| JP | 2000-204069 | | 7/2000 | |
| JP | 2002-87921 | | 3/2002 | |
| JP | 2013-544823 | | 12/2013 | |
| WO | 00/69394 | | 11/2000 | |
| WO | WO-0069394 A1 | * | 11/2000 | ........... A61K 6/0017 |
| WO | 2012/071329 | | 5/2012 | |
| WO | 2015/152220 | | 10/2015 | |

OTHER PUBLICATIONS

Extended European Search Report dated Jul. 24, 2018 in European Application No. 18153109.6.
Database Registry [Online] Chemical Abstracts Service, Columbus, Ohio, US; (Nov. 28, 2000), "2-Propenoic acid, 2-methyl-, 1,1'-(7-carboxy-7-methyl-4,10-dioxo-5,9-dioxa-3,11-diazatridecane-1,13-diyl) ester", XP002782752, Database accession No. 304698, 1 page.
Tanaka et al., "Development of High Strength, High Modulus, High Toughness Dental Matrix Resin without Environmental Endocrine Disruptor", Journal of the Japanese Association for Dental Science, vol. 24, 2005, pp. 51-60, with English Abstract.

* cited by examiner

*Primary Examiner* — Michael F Pepitone
(74) *Attorney, Agent, or Firm* — Wenderoth, Lind & Ponack, L.L.P.

(57) ABSTRACT

The present invention provides a dental curable composition comprising (A) a polymerizable monomer, (B) an inorganic filler, and (C) a polymerization initiator,
wherein the polymerizable monomer (A) comprises (a1) a polyfunctional (meth)acrylate monomer comprising urethane bonds, (a2) a polyfunctional (meth)acrylate monomer comprising hydroxyl groups, and (a3) a polyfunctional (meth)acrylate monomer comprising carboxyl groups,
the ratio by weight of (a1):(a2)+(a3) ranges from 1:1 to 9:1, the number of hydroxyl groups is not more than 0.5 relative to the number of (meth)acryloyl groups in one molecule of the above-mentioned (a2), and the number of carboxyl groups is not more than 0.5 relative to the number of (meth)acryloyl groups in one molecule of the above-mentioned (a3).

2 Claims, No Drawings

DENTAL CURABLE COMPOSITION HAVING HIGH MECHANICAL STRENGTH

TECHNICAL FIELD

The present invention relates to a dental curable composition used in dental filling restorative materials, dental crown prosthesis materials such as inlays, crowns, and bridges, materials for constructing anchor teeth, block materials for dental CAD/CAM, etc.

BACKGROUND ART

In dental treatments, dental curable compositions comprising polymerizable monomers, inorganic fillers and polymerization initiators have been widely used. These are generally called dental composite resins and utilized for various uses such as direct restorative materials for tooth defective parts due to dental caries, etc., dental crown prosthesis restorative materials such as inlays, crowns, and bridges, materials for constructing anchor tooth for dental crown defective parts, block materials for dental CAD/CAM, etc.

Dental restorations using the dental composite resins have a long history, and their ranges of use have been expanded. However, the mechanical properties of the dental composite resins are not still enough, and their actual condition is that an application to a part having high dental occlusion stress in an oral cavity (e.g., for dental crown materials for molar teeth) is restricted.

Furthermore, mechanical strength degradation of the dental composite resins in an oral cavity environment is regarded as problematic in recent years. Therefore, a development of the dental composite resins having the durability capable of maintaining mechanical strength over a long period of time under the severe environment in an oral cavity, has been desired.

Various characteristics needed for the dental composite resins are greatly affected to the molecular structures or combination composition of polymerizable monomers. The technological background of the polymerizable monomers which have been used for the dental composite resins is shown below.

In many cases, polyfunctional radical polymerizable (meth)acrylates are used as the polymerizable monomers to be used for the dental composite resins from viewpoints of safety in the body, the mechanical strength or abrasion wear resistance of cured products, etc. Combinations of 2,2-bis (4-(2-hydroxy-3-methacryloxypropoxy)phenyl)propane (hereinafter referred to as Bis-GMA), 1,6-bis(methacrylethyloxycarbonylamino)2,2,4-trimethylhexane (hereinafter referred to as UDMA), triethylene glycol dimethacrylate (hereinafter referred to as TEGDMA) are widely used as compositions of general polymerizable monomers. Dental composite resins which use these polymerizable monomers can be used without any problems as long as their application cases are limited. However, in the case that their application is expanded to a site to be subjected to high stress, such as a molar tooth, destruction and chipping of the dental composite resins had occurred since their mechanical strength was not enough.

Patent Documents 1 to 3 suggest methods for enhancing the mechanical strength of dental composite resins by using polymerizable monomers substituted for Bis-GMA or UDMA. However, even for dental composite resins of those inventions, their mechanical strength was not enough and there was a need for an improvement.

On the other hand, methods for considerably enhancing the mechanical strength of dental composite resins has been proposed by utilizing the hydrogen bonds between urethane bonds and hydroxyl groups included in polymerizable monomers. In Non-patent Document 1, a method for enhancing the mechanical strength of dental composite resins is proposed by using polymerizable monomers having urethane bonds, and monofunctional polymerizable monomers having carboxyl groups. However, although dental composite resins of this document conferred high mechanical strength to the dental composite resins, their aged deterioration in a water immersion environment was intense, and thereby there was a problem in their durability in an oral cavity environment.

Patent Document 4 proposes a method for enhancing the mechanical strength of dental composite resins by using polymerizable monomers having urethane bonds and polymerizable monomers having hydroxyl groups. However, although dental composite resins of this document conferred high mechanical strength to the dental composite resins, their aged deterioration under a water immersion environment was also intense, and thereby there was a problem in their durability in an oral cavity environment.

REFERENCE DOCUMENTS

Patent Documents

Patent Document 1: Japanese Publication Patent No. 2000-204069 A
Patent Document 2: Japanese Publication Patent No. 2013-544823 A
Patent Document 3: WO 2015/152220
Patent Document 4: Japanese Publication Patent No. 2002-87921 A

Non-Patent Documents

Non-patent Document 1: Journal of the Japanese Association for Dental Science, Vol. 24, pages 51-60 (2005)

SUMMARY OF THE INVENTION

Problems to Be Solved by the Invention

The object of the present invention is to provide a dental curable composition which is used in dental crown prosthesis materials such as inlays, crowns, and bridges, materials for constructing anchor tooth, block materials for dental CAD/CAM, etc., and which has an enhancement of a mechanical strength and a durability on aged deterioration in an oral cavity environment.

Means for Solving the Problems

The present inventors intensively studied the above-mentioned problems to accomplish them. As a result of the study, the inventors overcame those problems by providing a dental curable composition using polymerizable monomers, comprising (A) a polymerizable monomer, (B) an inorganic filler, and (C) a polymerization initiator, wherein the polymerizable monomer (A) comprises (a1) a polyfunctional (meth)acrylate monomer comprising urethane bonds, (a2) polyfunctional (meth)acrylate monomer comprising hydroxyl groups, and (a3) a polyfunctional (meth)acrylate monomer comprising carboxyl groups, the ratio by weight of (a1):(a2)+(a3) ranges from 1:1 to 9:1, the number of hydroxyl groups is not more than 0.5 relative to the number of (meth)acryloyl groups in one molecule of the above-mentioned (a2), the number of carboxyl groups is not more than 0.5 relative to the number of (meth)acryloyl groups in one molecule of the above-mentioned (a3). The present invention is based on the above-mentioned findings.

Effects of the Invention

The present invention can provide the dental curable composition having both of a mechanical strength capable of applying to a site where high dental occlusion stress is loaded in an oral cavity, and an aged deterioration capable of maintaining high mechanical strength for a long period of time under an underwater environment. The dental curable composition of the present invention is applicable to materials which need high mechanical strength and superior durability, such as dental filling restorative materials, dental crown prosthesis materials such as inlays, crowns, and bridges, materials for constructing anchor teeth, block materials for dental CAD/CAM, etc.

Modes for Carrying Out the Invention

The details of the present invention are explained below.

The present invention is a dental curable composition using polymerizable monomers, comprising (A) a polymerizable monomer, (B) an inorganic filler, and (C) a polymerization initiator, wherein the polymerizable monomer (A) comprises (a1) a polyfunctional (meth)acrylate monomer comprising urethane bonds, (a2) a polyfunctional (meth) acrylate monomer comprising hydroxyl groups, and (a3) a polyfunctional (meth)acrylate monomer comprising carboxyl groups, the ratio by weight of (a1):(a2)+(a3) ranges from 1:1 to 9:1, the number of hydroxyl groups is not more than 0.5 relative to the number of (meth)acryloyl groups in one molecule of the above-mentioned (a2), the number of carboxyl groups is not more than 0.5 relative to the number of (meth)acryloyl groups in one molecule of the above-mentioned (a3).

In the present invention, it is preferred that the viscosities of both the polyfunctional (meth)acrylate monomer comprising hydroxyl groups (a2) and the polyfunctional (meth) acrylate monomer comprising carboxyl groups (a3) are 10 to 1,000 mPa·s (25° C.).

In the present invention, it is preferred that the polyfunctional (meth)acrylate monomer comprising hydroxyl groups (a2) and the polyfunctional (meth)acrylate monomer comprising carboxyl groups (a3) comprise both of acryloyl groups and methacryloyl groups in one molecule.

The polyfunctional (meth)acrylate monomer comprising urethane bonds (a1) in the polymerizable monomer (A) to be used in the present invention, may be used from known polyfunctional polymerizable monomers comprising urethane bonds commonly used in the dental art without any restrictions. By illustrating a representative example which may be generally preferably used, it is a polymerizable monomer having acryloyl groups and/or methacryloyl groups. In addition, in the present invention, both of an acryloyl group-containing polymerizable monomer and a methacryloyl group-containing polymerizable monomer are comprehensively represented by (meth)acrylate or (meth) acryloyl groups.

Embodiments of the polyfunctional (meth)acrylate monomer comprising urethane bonds (a1) in the polymerizable monomer (A) to be used in the present invention, include a (meth)acrylate, etc. having urethane bonds induced from an adduct of a polymerizable monomer having hydroxyl groups such as 2-hydroxyethyl(meth)acrylate, 2-hydroxypropyl (meth)acrylate, or 3-chloro-2-hydroxypropyl(meth)acrylate and a diisocyanate compound such as methylcyclohexane-diisocyanate, methylenebis(4-cyclohexylisocyanate), hexamethylenediisocyanate, trimethylhexamethylenediisocyanate, isophoronediisocyanate, diisocyanatemethylmethylbenzene, or 4,4-diphenylmethanediisocyanate, and a (meth)acrylate, etc. having urethane bonds induced from a trimerisation reaction of a polymerizable monomer having hydroxyl groups such as 2-hydroxyethyl(meth)acrylate, 2-hydroxypropyl(meth)acrylate, or 3-chloro-2-hydroxypropyl(meth)acrylate and an isocyanurate ring.

The number of functional groups of the polyfunctional (meth)acrylate monomer comprising urethane bonds (a1) in the polymerizable monomer (A) to be used in the present invention is preferably 2 to 9 in functionality. When (a1) has one functionality, it is not preferred since a crosslinked structure is not formed and a sufficient mechanical strength cannot be conferred to the dental curable composition. On the other hand, when (a1) has a functionality of ten or more, it is not preferred since the density of its crosslinked structure becomes so high that it results in brittleness of the dental curable composition.

Molecular weight of the polyfunctional (meth)acrylate monomer comprising urethane bonds (a1) in the polymerizable monomer (A) to be used in the present invention is preferably not more than 5,000 g/mol. When the molecular weight of (a1) exceeds 5,000 g/mol, it is not preferred since the density of crosslinked structure becomes low and thereby a sufficient mechanical strength cannot be conferred to the dental curable composition.

The polyfunctional (meth)acrylate monomer comprising urethane bonds (a1) in the polymerizable monomer (A) to be used in the present invention is contained preferably at 50 to 90 parts by weight, and more preferably 60 to 80 parts by weight based on 100 parts by weight of the polymerizable monomer (A). When the content of (a1) is less than 50 parts by weight, it is not preferred since a sufficient mechanical strength cannot be conferred to a dental curable composition. On the other hand, when the content of (a1) exceeds 90 parts by weight, it is not preferred since its viscosity becomes so high that the operability of the dental curable composition is reduced.

The polymerizable monomer having acryloyl groups and/or methacryloyl groups which can be used as the polyfunctional (meth)acrylate monomer comprising hydroxyl groups (a2) to be used in the present invention is especially illustrated as follows.

Examples of the polyfunctional (meth)acrylate monomer comprising hydroxyl groups (a2) to be used in the present invention include glycerin dimethacrylate, 2-butyl-2-ethyl-1,3-propanediol di(meth)acrylate, and isocyanuric acid EO-denatured diacrylate.

The polyfunctional (meth)acrylate monomer comprising hydroxyl groups (a2) to be used in the present invention is preferably a monomer comprising both of acryloyl groups and methacryloyl groups in one molecule of (a2). Specifically, examples of the polyfunctional (meth)acrylate monomer include 2-hydroxy-3-acryloyloxy propyl methacrylate, and 1-(acryloyloxy)-3-(methacryloyloxy)-2-propanol.

The number of functional groups of the polyfunctional (meth)acrylate monomer comprising hydroxyl groups (a2) to be used in the present invention is preferably 2 to 9 in functionality. When (a2) has one functionality, it is not preferred since a crosslinked structure is not formed and a sufficient mechanical strength cannot be conferred to the dental curable composition. On the other hand, when (a2) has a functionality of ten or more, it is not preferred since the density of its crosslinked structure becomes so high that it results in brittleness of the dental curable composition.

Molecular weight of the polyfunctional (meth)acrylate monomer comprising hydroxyl groups (a2) in the polymerizable monomer (A) to be used in the present invention is preferably not more than 1,000 g/mol. When the molecular weight of (a2) exceeds 1,000 g/mol, it is not preferred since the density of crosslinked structure becomes low and thereby a sufficient mechanical strength cannot be conferred to the dental curable composition.

Viscosity of the polyfunctional (meth)acrylate monomer comprising hydroxyl groups (a2) to be used in the present invention preferably ranges from 10 to 1,000 mPa·s (25° C.), and more preferably from 15 to 800 mPa·s (25° C.).

The polyfunctional (meth)acrylate monomer comprising hydroxyl groups (a2) to be used in the present invention is contained at 5 to 50 parts by weight, preferably 10 to 40 parts by weight, and more preferably 20 to 30 parts by weight based on 100 parts by weight of the polymerizable monomer (A). When the content of (a2) is less than 5 parts by weight, it is not preferred since a sufficient toughness cannot be conferred to the crosslinked structure and a sufficient mechanical strength cannot be conferred to the dental curable composition. On the other hand, when the content of (a2) exceeds 50 parts by weight, it is not preferred since an amount of water absorption increases and a durability under an underwater environment decreases.

The polymerizable monomer having acryloyl groups and/or methacryloyl groups which can be used as the a polyfunctional (meth)acrylate monomer comprising carboxyl groups (a3) to be used in the present invention is especially illustrated as follows.

Examples of the polyfunctional (meth)acrylate monomer comprising carboxyl groups (a3) to be used in the present invention include a reaction mixture of glycerin dimethacrylate and succinic anhydride, and a reactant of glycerin dimethacrylate and phthalic anhydride.

As the polyfunctional (meth)acrylate monomer comprising carboxyl groups (a3) to be used in the present invention, a monomer comprising both of acryloyl groups and methacryloyl groups in one molecule may be particularly preferably used. Specifically, examples of the polyfunctional (meth)acrylate monomer include a reaction mixture of 2-hydroxy-3-acryloyloxy propyl methacrylate and succinic anhydride, and a reactant of 2-hydroxy-3-acryloyloxy propyl methacrylate and phthalic anhydride.

It is preferred that the number of functional groups of the polyfunctional (meth)acrylate monomer comprising carboxyl groups (a3) to be used in the present invention is 2 to 9 in functionality. When (a3) has one functionality, it is not preferred since a crosslinked structure is not formed and a sufficient mechanical strength cannot be conferred to the dental curable composition. On the other hand, when the functionality of (a3) exceeds ten functionalities, it is not preferred since the density of its crosslinked structure becomes too high that it results in brittleness of the dental curable composition.

Molecular weight of the polyfunctional (meth)acrylate monomer comprising carboxyl groups (a3) in the polymerizable monomer (A) to be used in the present invention is preferably not more than 1,000 g/mol. When the molecular weight of (a3) exceeds 1,000 g/mol, it is not preferred since the density of crosslinked structure becomes low and thereby a sufficient mechanical strength cannot be conferred to the dental curable composition.

Viscosity of the polyfunctional (meth)acrylate monomer comprising carboxyl groups (a3) to be used in the dental curable composition of the present invention preferably ranges from 10 to 1,000 mPa·s (25° C.), and more preferably from 15 to 800 mPa·s (25° C.).

The polyfunctional (meth)acrylate monomer comprising carboxyl groups (a3) to be used in the present invention is contained preferably at 1 to 30 parts by weight, and more preferably at 5 to 15 parts by weight based on 100 parts by weight of the polymerizable monomer (A). When the content of (a3) is less than 1 part by weight, it is not preferred since a sufficient toughness cannot be conferred to the crosslinked structure and a sufficient mechanical strength cannot be conferred to the dental curable composition. On the other hand, when the content of (a3) exceeds 30 parts by weight, it is not preferred since its amount of water absorption increases and its durability under an underwater environment decreases.

The present invention can confer a suitable rigidity and toughness to the crosslinked structure to exert a superior mechanical strength in the dental curable composition by optimizing the ratio of primary bonds consisting of covalent bonds of (meth)acryloyl groups to secondary bonds consisting of hydrogen bonds of urethane bonds and hydroxy groups (hydroxyl groups, carboxyl groups).

The present invention can be accomplished by optimizing (a1):(a2)+(a3) which is the ratio by weight of the polyfunctional (meth)acrylate monomer comprising urethane bonds (a1), the polyfunctional (meth)acrylate monomer comprising hydroxyl groups (a2), and the polyfunctional (meth)acrylate monomer comprising carboxyl groups (a3) in the polymerizable monomer (A) to be used in the present invention. Specifically, it is preferred that the above-mentioned ratio by weight of (a1):(a2)+(a3) ranges from 1:1 to 9:1. When (a1) exceeds 9 in the case of (a2)+(a3)=1, namely, when urethane bonds are too excessive to hydroxyl groups and carboxyl groups in their weights, sufficient toughness due to hydrogen bonds between hydroxyl groups and urethane bonds, or carboxyl groups and urethane bonds cannot be conferred and thereby it is not preferred since a superior mechanical strength cannot be conferred to the dental curable composition. On the other hand, when (a1) becomes less than 1 in the case of (a2)+(a3)=1, namely, when urethane bonds are too small against hydroxyl groups and carboxyl groups in their weights, it is not preferred since the durability of the dental curable composition is reduced under an underwater environment.

Furthermore, the present invention can confer a superior durability to the dental curable composition by optimizing the ratio of hydrogen bonds relative to covalent bonds in crosslinked structure.

Specifically, the polyfunctional (meth)acrylate monomer comprising hydroxyl groups (a2) to be used in the present invention is characterized in that the number of hydroxyl groups is not more than 0.5 relative to the number of (meth)acryloyl groups in one molecule of (a2). When the above-mentioned number of hydroxyl groups/number of (meth)acryloyl groups exceeds 0.5, it is not preferred since hydroxyl groups are excess, water absorbency of the dental curable composition increases and its durability under an underwater environment decreases.

Similarly, the polyfunctional (meth)acrylate monomer comprising carboxyl groups (a3) in the polymerizable monomer (A) to be used in the present invention is characterized in that the number of carboxyl groups is not more than 0.5 relative to the number of (meth)acryloyl groups in one molecule of (a3). When the above-mentioned number of carboxyl groups/number of (meth)acryloyl groups exceeds 0.5, it is not preferred since carboxyl groups are excess, water absorbency of the dental curable composition increases and its durability under an underwater environment decreases.

The known fillers which are commonly used can be used as an inorganic filler (B) in the present invention.

By illustrating the inorganic filler (B) to be used in the present invention, its specific examples include silica, aluminum silicate, alumina, titania, zirconia, various glasses (including fluoride glass, borosilicate glass, soda glass, barium glass, barium aluminum silica glass, glass including strontium or zirconium, glass ceramics, fluoroaluminosilicate glass, and synthetic glass by a sol-gel method), Aerosil (registered trademark), calcium fluoride, strontium fluoride, calcium carbonate, kaolin, clay, mica, aluminum sulfate, calcium sulfate, barium sulfate, titanium oxide, calcium phosphate, hydroxyapatite, calcium hydroxide, strontium hydroxide and zeolite. These inorganic fillers may be used as an aggregate, and examples of the aggregate include a silica-zirconia composite oxide aggregate obtained by mixing a silica sol and a zirconia sol and then spray-drying and heat-treating the mixture.

A filler having any shape, such as a spherical shape, a needle shape, a plate shape, a crushed shape or a scale shape, may be used as the inorganic filler (B) to be used in the present invention. The average particle size of the inorganic filler (B) varies depending on the type of the filler, and for the inorganic-based filler, any filler may be used as long as the filler has an average particle size ranging from 0.05 to 200 µm, preferably ranging from 0.5 to 100 µm, and more preferably ranging from 1 to 20 µm. When the inorganic filler (B) is an aggregate, the above-mentioned average particle size is an average particle size of the aggregate. When the inorganic filler is an aggregate, its average particle size is preferably from 0.5 to 100 µm, and more preferably from 1 to 20 µm. In addition, the information on the average particle size, coefficient of variation of particle sizes, etc. can be investigated by a laser diffraction type particle size measuring machine. When the average particle size of the inorganic filler is less than 0.05 µm, it is not preferred since the dental curable composition is sticky and its operability decreases. On the other hand, when the average particle size of the inorganic filler (B) is more than 200 µm, it is not preferred since the mechanical strength of the dental curable composition is reduced.

The surface of the inorganic filler (B) to be used in the present invention may be multi-functionalized by a surface treatment method using surface treatment agent(s), etc., and these surface treatment agents can be used without any restrictions. By illustrating the surface treatment agent to be used to multi-functionalize the surface of the inorganic filler, their specific examples include a surfactant, a fatty acid, an organic acid, an inorganic acid, various coupling materials (a titanate coupling agent, an aluminate coupling agent and a silane coupling agent), and a metal alkoxide compound. By illustrating the surface treatment method, its specific examples include a method of spraying the surface treatment agent in the state of allowing the filler to flow, a method of dispersing the filler in a solution including the surface treatment agent, and a method of multilayering several kinds of surface treatment agents on the surface of the inorganic filler. The surface treatment agent and the surface treatment method, however, are not limited thereto. Moreover, each of these surface treatment agents or surface treatment methods can be used alone or in a composite combination.

The content of the inorganic filler (B) to be used in the present invention is not particularly limited, but the content thereof in the dental curable composition is preferably 60 to 90 parts by weight, and more preferably 70 to 90 parts by weight. When the content of the inorganic filler (B) is less than 60 parts by weight, a sufficient mechanical strength cannot be obtained, and when the content is more than 90 parts by weight, it is not preferred since it is difficult to obtain a dental curable composition in which the filler is uniformly dispersed.

In the dental curable composition of the present invention, various kinds of known fillers may be combined, if necessary. Examples of the filler to be used in the present invention include an organic filler and an organic-inorganic composite filler.

Examples of the organic filler include, but not limited to, elastomers such as polyvinyl acetate, polyvinyl alcohol and a styrene-butadiene rubber, non-crosslinkable (meth)acrylate polymers each being a homopolymer of a monofunctional (meth)acrylate polymerizable monomer, such as polymethyl methacrylate (PMMA), polyethyl methacrylate, polypropyl methacrylate and polybutyl methacrylate, crosslinkable (meth)acrylate polymers obtained by copolymerizing a monofunctional (meth)acrylate polymerizable monomer with a polymerizable monomer having two or more functional groups, and polyvinyl acetate, polyethylene glycol, polypropylene glycol and polyvinyl alcohol.

Examples of the organic-inorganic composite filler include, but not at all limited to, one obtained by polymerizing a polymerizable monomer on and covering the surface of a filler, one obtained by mixing and polymerizing a filler and a polymerization monomer, and then grinding the resultant mass to a proper particle size, or one obtained from an emulsion polymerization or suspension polymerization by dispersing a filler in a polymerizable monomer in advance.

The polymerization initiator (C) to be used in the present invention is not particularly limited, and a known radical generator may be used as the polymerization initiator without any restrictions. The polymerization initiator is roughly classified into an initiator which is mixed immediately before use to initiate a polymerization (chemical polymerization initiator), an initiator which initiates a polymerization by heating (thermal polymerization initiator), and an initiator which initiates a polymerization by light irradiation (photo-polymerization initiator).

Examples of the chemical polymerization initiator include a redox type polymerization initiator comprising an organic peroxide/amine compound, an organic peroxide/amine compound/sulfinate, or an organic peroxide/amine compound/borate compound; and an organometal type polymerization initiator which reacts with oxygen or water to initiate a polymerization. Sulfinates and borate compounds can also initiate a polymerization by reacting them with a polymerizable monomer having an acidic group.

By illustrating the organic peroxide, its specific examples include benzoyl peroxide, parachlorobenzoyl peroxide, 2,4-dichlorobenzoyl peroxide, acetyl peroxide, lauroyl peroxide, tertiary butyl peroxide, cumene hydroperoxide, 2,5-dimethylhexane, 2,5-dihydroperoxide, methyl ethyl ketone peroxide and tertiary butylperoxybenzoate.

The amine compound is preferably a secondary or tertiary amine in which an amine group is bound to an aryl group. By illustrating the amine compound, its specific examples include p-N,N-dimethyl-toluidine, N,N-dimethylaniline, N-β-hydroxyethyl-aniline, N,N-di(β-hydroxyethyl)-aniline, p-N,N-di(β-hydroxyethyl)-toluidine, N-methyl-aniline and p-N-methyl-toluidine. By illustrating the sulfinates, their specific examples include sodium benzenesulfinate, lithium benzenesulfinate and sodium p-toluenesulfinate.

Examples of the borate compound include sodium salts, lithium salts, potassium salts, magnesium salts, tetrabutylammonium salts and tetramethylammonium salts of trialkylphenylboron and trialkyl(p-fluorophenyl)boron (an alkyl group is a n-butyl group, a n-octyl group, a n-dodecyl group, etc.).

Examples of the organometal type polymerization initiator include organic boron compounds such as triphenylborane, tributylborane and tributylborane partial oxide.

Organic peroxides may be preferably used as the thermal polymerization initiator. Specific examples of the organic peroxides include benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethylhexane, 2,5-dihydroperoxide, methyl ethyl ketone peroxide and tertiarybutylperoxybenzoate.

Examples of the photo-polymerization initiator include one made of photosensitizers, and photosensitizers/photopolymerization promoters. By illustrating the photosensitizers, their specific examples include α-diketones such as benzyl, camphor quinone, α-naphthyl, acetonaphthene, p,p'-dimethoxybenzyl, dichlorobenzylacetyl, pentanedione, 1,2-phenanthrenequinone, 1,4-phenanthrenequinone, 3,4-phenanthrenequinone, 9,10-phenanthrenequinone and naphthoquinone, benzoin alkyl ethers such as benzoin, benzoin methyl ether and benzoin ethyl ether, thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone, benzophenones such as benzophenone, p-chlorobenzophenone and p-methoxybenzophenone, acylphosphine oxides such as 2,4,6-trimethylbenzoyl diphenylphosphine oxide and bis(2,6-dimethoxybenzoyl)-2,4,4-trimethylpentylphosphine oxide, α-aminoacetophenones such as 2-benzyl-dimethylamino-1-(4-morpholinophenyl)-butanone-1,2-benzyl-diethylamino-1-(4-morpholinophenyl)-propanone-1, ketals such as benzyl dimethyl ketal, benzyl diethyl ketal and benzyl(2-methoxyethyl ketal), and titanocenes such as bis(cyclopentadienyl)-bis[2,6-difluoro-3-(1-pyrrolyl)phenyl]-titanium, bis(cyclopentadienyl)-bis(pentanefluorophenyl)-titanium and bis(cyclopentadienyl)-bis(2,3,5,6-tetrafluoro-4-disiloxyphenyl)-titanium.

By illustrating the photopolymerization promoters, their specific examples include tertiary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, p-N,N-dihydroxyethyl-toluidine, p-dimethylaminophenyl alcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino)diethanol, secondary amines such as N-phenylglycine, barbituric acids such as 5-butylbarbituric acid and 1-benzyl-5-phenylbarbituric acid, tin compounds such as dibutyl tin diacetate, dibutyl tin dilaurate, dioctyl tin dilaurate, dioctyl tin diversatate, dioctyl tin bis(mercaptoacetic acid isooctyl ester) salt and tetramethyl-1,3-diacetoxydistannoxane, aldehyde compounds such as laurylaldehyde and terephthalaldehyde, and sulfur-containing compounds such as dodecylmercaptan, 2-mercaptobenzoxazole, 1-decanethiol and thiosalicylic acid.

In order to enhance photopolymerization promotion performances, it is effective to add oxycarboxylic acids such as citric acid, malic acid, tartaric acid, glycolic acid, gluconic acid, a-oxyisobutyric acid, 2-hydroxypropanoic acid, 3-hydroxypropanoic acid, 3-hydroxybutanoic acid, 4-hydroxybutanoic acid and dimethylolpropionic acid in addition to the above-mentioned photopolymerization promoter.

These polymerization initiators may be used alone or in combinations of two or more, regardless of the polymerization manner or polymerization method. In addition, there is no problem even if these polymerization initiators are subjected to a secondary treatment such as encapsulation in a microcapsule, if necessary.

The content of the polymerization initiator (C) to be used in the present invention may be appropriately selected depending on the application, and the content preferably ranges from 0.01 to 10 parts by weight, more preferably from 0.1 to 5 parts by weight based on 100 parts by weight of the polymerizable monomers.

To the curable dental composition of the present invention, various known additives may be added, if necessary. Examples of the additives to be used in the present invention include a polymerization inhibitor, a chain transfer agent, a coloring agent, a discoloration inhibitor, a fluorescent agent, an ultraviolet absorber, and an antibacterial agent.

EXAMPLES

Although Examples of the present invention are specifically described below, the present invention is not intended to be limited to these Examples. The test methods in Examples and Comparative Examples are described below.

Abbreviations and properties of the polyfunctional (meth)acrylate monomers comprising urethane bonds (a1) used in preparations of the curable dental composition are shown as follows:

UDMA: 1,6-Bis(methacrylethyloxycarbonylamino)2,2,4-trimethylhexane, bifunctional urethane monomer, Molecular weight: 470

9UA: Nonifunctional urethane acrylate oligomer, Molecular weight: 760

Abbreviations and properties of the (meth)acrylate monomer comprising hydroxyl groups (a2) used in preparations of the curable dental composition are shown as follows:

GDMA: Glycerin dimethacrylate, hydroxyl groups/(meth)acrylate groups=0.5, Viscosity: 40 mPa·s (25° C.)

TRPA: Pentafunctional dipentaerythritol pentaacrylate, hydroxyl groups/(meth)acrylate groups=0.2, Viscosity: 40 mPa·s (25° C.)

AHMA: 2-Hydroxy-3-acryloyloxy propyl methacrylate, hydroxyl groups/(meth)acrylate groups=0.5, Viscosity: 40 mPa·s (25° C.)

Abbreviations and properties of the (meth)acrylate monomers comprising carboxyl groups (a3) used in preparations of the curable dental composition are shown as follows:

GDSU: Reactant of glycerin dimethacrylate and succinic anhydride, carboxyl groups/(meth)acrylate groups=0.5, Viscosity: 40 mPa·s (25° C.)

TRSU: Reactant of pentafunctional dipentaerythritol pentaacrylate and succinic anhydride, carboxyl groups/(meth)acrylate groups=0.2, Viscosity: 40 mPa·s (25° C.)

AHSU: Reactant of 2-hydroxy-3-acryloyloxy propyl methacrylate and succinic anhydride, carboxyl groups/(meth)acrylate groups=0.5, Viscosity: 40 mPa·s (25° C.)

Abbreviations of the other monomers used in preparations of the curable dental composition are shown as follows:

Bis-GMA: 2,2-bis(4-(2-hydroxy-3-methacryloxy-propoxy) phenyl)propane, hydroxyl groups/(meth)acrylate groups=1.0, Viscosity: about 0.1 millions mPa·s (25° C.)

TEGDMA: Triethylene glycol dimethacrylate, Viscosity: 9 mPa·s (25° C.)

HEMA: 2-Hydroxyethyl methacrylate, hydroxyl groups/(meth)acrylate groups=1.0, Viscosity: 6 mPa·s (25° C.)

MA: Methacrylic acid, carboxyl groups/(meth)acrylate groups=1.0, Viscosity: 1 mPa·s (25° C.)

Abbreviations of inorganic fillers used in preparations of the curable dental composition are shown as follows:

SPF: Spherical shape of silica fillers ($d_{50}$: 1 µm)

NSF: Amorphous shape of silica fillers ($d_{50}$: 3 µm)

Abbreviations of polymerization initiator (C) used in preparations of the curable dental composition are shown as follows:

CQ: Camphor quinone

DMBE: Ethyl dimethylaminobenzoate

BPO: Benzoyl peroxide (1) Measurements of Bending Strength (1-1) Preparations of Bending Strength Test Samples (Photopolymerization)

Methods: After filling up a metallic mold made from stainless steel (25×2×2 mm: rectangular parallelepiped type) with a curable dental composition to be subjected to the test, covergrasses are placed at both sides of the metallic mold and pressure-welded with a glass slab. Subsequently, a photopolymerization irradiator (Solidilite V: manufactured by SHOFU, Inc.) is used to cure the front surface and the back surface of the composition by light-irradiating them for 3 minutes each. After its cured material was removed from the metallic mold, the cured material was subjected to a thermal polymerization (110° C., 15 min) using a thermal polymerization device.

(1-2) Preparations of Bending Strength Test Samples (Thermal Polymerization)

Methods: After filling up a metallic mold made from stainless steel (25×2×2 mm: rectangular parallelepiped type) with a curable dental composition to be subjected to the test, the composition was pressurized and heat-molded at a condition of press pressure on metallic mold: 3t, molding temperature: 100° C., and press time: 10 min.

(1-3) Methods of Bending Test

Methods: Measurement of bending strength in this test is performed with Instron Universal Testing Machine (Instron 5567: manufactured by Instron company) and at a distance between fulcrums of 20 mm and a crosshead speed of 1 mm/min.

(2) Evaluation of Aged Deterioration (2-1) Initial Bending Strength

Methods: After each of test samples is immersed into water (at 37° C. for 24 hours), its bending strength was measured. This was made an initial bending strength.

(2-2) Bending Strength after Thermal Cycling

Methods: After each of test samples is immersed into water (at 37° C. for 24 hours), each of test samples is subjected to a thermal cycle test (in water at 4° C. to 60° C., immersion during 1 minute each, 2,000 times), and subsequently its bending strengths was measured. This was made a bending strength after thermal cycling.

(2-3) Bending Strength Maintenance Rate

Methods: In order to evaluate durability by aged deterioration for each of the test samples, its strength maintenance rate was calculated according to the following formula:

$$\text{Bending strength maintenance rate} = (\text{bending strength after thermal cycling})/(\text{initial bending strength}) \times 100$$

(3) Measurement of Amount of Water Absorption (3-1) Preparation of Test Samples for Amount of Water Absorption (photopolymerization)

Methods: After filling up a metallic mold made from stainless steel (15 mm in diameter×1 mm in thickness) with a curable dental composition to be subjected to the test, covergrasses are placed at both sides of the metallic mold and pressure-welded with a glass slab. Subsequently, the photopolymerization irradiator (Solidilite V: manufactured by SHOFU, Inc.) is used to cure the front surface and the back surface of the composition by light-irradiating them for 3 minutes each. After its cured material was removed from the metallic mold, the cured material was subjected to a thermal polymerization (110° C., 15 min) using a thermal polymerization device.

(3-2) Preparation of Test Samples for Amount of Water Absorption (Thermal Polymerization)

Methods: After filling up a metallic mold made from stainless steel (15 mm in diameter×1 mm in thickness) with a curable dental composition to be subjected to the test, the composition was pressurized and heat-molded at a condition of press pressure on metallic mold: 3t, molding temperature: 100° C., and press time: 10 min.

(3-3) Test Method of Amount of Water Absorption

Test method of amount of water absorption was carried out according to JIS T6517 (dental hard resin). Each of test samples was preserved in a desiccator, and weighted in 0.1 mg unit. Until the test samples have a decreased mass of less than 0.1 mg within 24 hours, the test samples were continued to be dried and weighted by repeating these operations, and final masses of dried test samples were made $m_1$. Then, after the test samples were preserved in water at 37° C. for 7 days, masses of the water-absorbed test samples were made $m_2$. The amount of water absorption of each of the test samples was calculated according to the following formula:

$$\text{Amount of water absorption} = (\text{mass } m_2 \text{ of water-absorbed test sample} - \text{mass } m_1 \text{ of dried test sample})/\text{volume of test sample}$$

Preparation of Binder Resins (R-1 to R-16)

Binder resins were prepared by mixing in the compositions as shown in Table 1.

TABLE 1

| | Ingredients | R-1 | R-2 | R-3 | R-4 | R-5 | R-6 | R-7 | R-8 | R-9 | R-10 | R-11 | R-12 | R-13 | R-14 | R-15 | R-16 | R-17 |
|---|---|---|---|---|---|---|---|---|---|---|---|---|---|---|---|---|---|---|
| (a1) Polyfunctional (meth)acrylate monomer comprising urethane bonds | UDAM 9UA | 50 | 80 | 89 | 75 | 87.5 | 80 | 80 | 80 | 80 | 80 | 40 | 95 | 80 | 80 | 80 | 70 | 80 |
| (a2) Polyfunctional (meth)acrylate monomer comprising hydroxyl groups | GDMA TRPA AHMA | 49 | 15 | 10 | 15 | 5 | 15 | 15 | 15 | 15 | 15 | 30 | 2 | | 15 | | | |
| (a3) Polyfunctional (meth)acrylate monomer comprising carboxyl groups | GDSU M-405S AHSU | 1 | 5 | 1 | 10 | 7.5 | 5 | 5 | 5 | 5 | 5 | 30 | 3 | 5 | | | | 5 |
| Others | Bis-GMA TEGDMA HEMA MA | | | | | | | | | | | | | 15 | 20 | 5 | 30 | 15 |
| (C) Polymerization initiator | CQ DMBE BPO | 0.3 2 | 0.3 2 | 0.3 2 | 0.3 2 | 0.3 2 | 0.3 2 | 0.3 2 | 0.3 2 | 0.3 | 0.3 | 0.3 2 | 0.3 2 | 0.3 2 | 0.3 2 | 0.3 2 | 0.3 2 | 0.3 2 |

Preparation of Inorganic Filler (B-1)

SPF (100 parts by weight) was surface-treated with γ-methacryloxy propyltrimethoxy silane (10 parts by weight) to obtain an inorganic filler (B-1).

Preparation of Inorganic Filler (B-2)

NSF (100 parts by weight) was surface-treated with γ-methacryloxy propyltrimethoxy silane (3 parts by weight) to obtain an inorganic filler (B-2).

Production methods of the dental curable compositions used in Examples and Comparative Examples are shown below.

Example 1

Binder resin (R-1): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Example 2

Binder resin (R-2): 30 parts by weight, Inorganic filler (B-1): 85 parts by weight, and AEROSIL R-972 (hydrophobized ultrafine particles of silicon dioxide): 1 part by weight were kneaded with a double planetary mixer and vacuum-degassed to obtain a dental curable composition.

Example 3

Binder resin (R-3): 30 parts by weight, Inorganic filler (B-1): 70 parts by weight, and AEROSIL R-972 (hydrophobized ultrafine particles of silicon dioxide): 1 part by weight were kneaded with a double planetary mixer and vacuum-degassed to obtain a dental curable composition.

Example 4

Binder resin (R-4): 30 parts by weight, Inorganic filler (B-1): 85 parts by weight, and AEROSIL R-972 (hydrophobized ultrafine particles of silicon dioxide): 1 part by weight were kneaded with a double planetary mixer and vacuum-degassed to obtain a dental curable composition.

Example 5

Binder resin (R-5): 30 parts by weight, Inorganic filler (B-1): 90 parts by weight, and AEROSIL R-972 (hydrophobized ultrafine particles of silicon dioxide): 1 part by weight were kneaded with a double planetary mixer and vacuum-degassed to obtain a dental curable composition.

Example 6

Binder resin (R-6): 30 parts by weight, Inorganic filler (B-2): 80 parts by weight, and AEROSIL R-972 (hydrophobized ultrafine particles of silicon dioxide): 1 part by weight were kneaded with a double planetary mixer and vacuum-degassed to obtain a dental curable composition.

Example 7

Binder resin (R-7): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Example 8

Binder resin (R-8): 30 parts by weight, Inorganic filler (B-2): 80 parts by weight, and AEROSIL R-972 (hydrophobized ultrafine particles of silicon dioxide): 1 part by weight were kneaded with a double planetary mixer and vacuum-degassed to obtain a dental curable composition.

Example 9

Binder resin (R-9): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Example 10

Binder resin (R-10): 30 parts by weight, Inorganic filler (B-2): 80 parts by weight, and AEROSIL R-972 (hydrophobized ultrafine particles of silicon dioxide): 1 part by weight were kneaded with a double planetary mixer and vacuum-degassed to obtain a dental curable composition.

Example 11

Binder resin (R-2): 30 parts by weight, Inorganic filler (B-1): 60 parts by weight, and AEROSIL R-972 (hydrophobized ultrafine particles of silicon dioxide): 1 part by weight were kneaded with a double planetary mixer and vacuum-degassed to obtain a dental curable composition.

Example 12

Binder resin (R-2): 30 parts by weight, Inorganic filler (B-1): 90 parts by weight, and AEROSIL R-972 (hydrophobized ultrafine particles of silicon dioxide): 1 part by weight were kneaded with a double planetary mixer and vacuum-degassed to obtain a dental curable composition.

Comparative Example 1

Binder resin (R-11): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Comparative Example 2

Binder resin (R-12): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Comparative Example 3

Binder resin (R-13): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Comparative Example 4

Binder resin (R-14): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Comparative Example 5

Binder resin (R-15): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

Comparative Example 6

Binder resin (R-16): 30 parts by weight, Inorganic filler (B-1): 80 parts by weight, and AEROSIL R-972 (hydrophobized ultrafine particles of silicon dioxide): 1 part by weight were kneaded with a double planetary mixer and vacuum-degassed to obtain a dental curable composition.

The physical property test results of the prepared dental curable compositions are shown in Tables 2 and 3.

TABLE 2

| | | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|---|
| Binder resin | Names | R-1 | R-2 | R-3 | R-4 | R-5 | R-6 | R-7 | R-8 | R-9 | R-10 | R-2 | R-2 |
| | (a1):(a2) + (a3) | 1:1 | 4:1 | 89:11 | 3:1 | 7:1 | 4:1 | 4:1 | 4:1 | 4:1 | 4:1 | 4:1 | 4:1 |
| | Number of hydroxyl groups/number of (meth)acryloyl groups | 0.5 | 0.5 | 0.5 | 0.5 | 0.5 | 0.2 | 0.5 | 0.5 | 0.5 | 0.5 | 0.5 | 0.5 |
| | Number of carboxyl groups/number of (math)acryloyl groups | 0.5 | 0.5 | 0.5 | 0.5 | 0.5 | 0.2 | 0.5 | 0.5 | 0.5 | 0.5 | 0.5 | 0.5 |
| Inorganic filler | Names | B-1 | B-1 | B-1 | B-1 | B-1 | B-2 | B-1 | B-2 | B-1 | B-2 | B-1 | B-1 |
| Bending strength | Initial (MPa) | 230 | 244 | 240 | 248 | 233 | 243 | 251 | 253 | 232 | 222 | 219 | 233 |
| | After thermal cycling (MPa) | 207 | 220 | 229 | 224 | 211 | 225 | 237 | 241 | 221 | 211 | 209 | 218 |
| | Bending strength maintenance rate (%) | 90 | 90.2 | 95.4 | 90.3 | 90.6 | 92.6 | 94.4 | 95.3 | 95.3 | 95 | 95.4 | 93.6 |
| Amount of water absorption | Amount of water absorption (μg/mm³) | 30 | 29 | 29 | 30 | 29 | 30 | 27 | 28 | 29 | 30 | 27 | 30 |

TABLE 3

| | | Comparative Example 1 | Comparative Example 2 | Comparative Example 3 | Comparative Example 4 | Comparative Example 5 | Comparative Example 6 | Conparative Example 7 |
|---|---|---|---|---|---|---|---|---|
| Binder resin | Names | R-11 | R-12 | R-13 | R-14 | R-15 | R-16 | R-17 |
| | (a1):(a2) + (a3) | 2:3 | 19:1 | 4:1 | — | 4:1 | — | — |
| | Number of hydroxyl groups/number of (meth)acryloyl groups | 0.5 | 0.5 | 1.0 | 0.5 | 1.0 | — | — |
| | Number of carboxyl groups/number of (meth) acryloyl groups | 0.5 | 0.5 | 0.5 | 1.0 | — | — | — |
| Inorganic | Names | B-1 | B-1 | B-1 | B-1 | B-1 | B-1 | B-1 |
| Bending strength | Initial (MPa) | 196 | 188 | 231 | 229 | 199 | 180 | 220 |
| | After thermal cycling (MPa) | 166 | 159 | 198 | 187 | 176 | 161 | 179 |
| | Bending strength maintenance rate (%) | 84.7 | 84.6 | 85.7 | 81.7 | 88.4 | 89.4 | 81.4 |
| Amount of water absorption | Amount of water absorption (µg/mm³) | 34 | 33 | 35 | 34 | 35 | 29 | 35 |

Examples 1-12

The dental curable compositions of Examples 1-12 had the ratio by weight of (a1):(a2)+(a3) ranged from 1:1 to 1:9, the number of hydroxyl groups/number of (meth)acryloyl groups in (a2) of not more than 0.5, and the number of carboxyl groups/number of (meth)acryloyl groups in (a3) of not more than 0.5.

As a result, it was recognized that the dental curable compositions of Examples 1-12 had high bending strengths at the initial point and after thermal cyclings, and also had both of superior mechanical strengths and durabilities.

Comparative Examples 1 And 2

The dental curable compositions of Comparative Examples 1 and 2 have used monomers having the number of hydroxyl groups/number of (meth)acryloyl groups in (a2) of not more than 0.5, and the number of carboxyl groups/number of (meth)acryloyl groups in (a3) of not more than 0.5. However, the ratios by weight of (a1):(a2)+(a3) do not range from 1:1 to 1:9. Therefore, although the compositions had high initial bending strengths, their bending strengths after the thermal cycling were poor and thereby it was recognized that the compositions had poor durability.

Comparative Example 3

The dental curable composition of Comparative Example 3 had the ratio by weight of (a1):(a2)+(a3) ranged from 1:1 to 1:9. However, the number of hydroxyl groups/number of (meth)acryloyl groups in (a2) was 0.6 or more, and the initial bending strength was high, whereas the bending strength after the thermal cycling was low. Therefore, it was recognized that its durability was poor.

Comparative Example 4

The dental curable composition of Comparative Example 4 had the ratio by weight of (a1):(a2)+(a3) ranged from 1:1 to 1:9. However, the number of carboxyl groups/number of (meth)acryloyl groups in (a3) was 0.6 or more, and the initial bending strength was high, whereas the bending strength after the thermal cycling was low. Therefore, it was recognized that its durability was poor.

Comparative Example 5

The dental curable composition of Comparative Example 5 had the ratio by weight of (a1):(a2)+(a3) ranged from 1:1 to 1:9. However, both of the number of hydroxyl groups/number of (meth)acryloyl groups in (a2) and the number of carboxyl groups/number of (meth)acryloyl groups in (a3) were 0.6 or more, and the initial bending strength was high, whereas the bending strength after the thermal cycling was low. Therefore, it was recognized that its durability was poor.

Comparative Example 6

The dental curable composition of Comparative Example 6 had a composition of common binder resins, and it was recognized that the bending strengths at the initial point and after the thermal cycling were low.

The invention claimed is:

1. A dental curable composition comprising (A) a polymerizable monomer, (B) an inorganic filler, and (C) a polymerization initiator,
   wherein the polymerizable monomer (A) comprises (a1) a polyfunctional (meth)acrylate monomer comprising urethane bonds, (a2) a polyfunctional (meth)acrylate monomer comprising hydroxyl groups, and (a3) a polyfunctional (meth)acrylate monomer comprising carboxyl groups,
   the ratio by weight of (a1):(a2)+(a3) ranges from 1:1 to 9:1, the number of hydroxyl groups is not more than 0.5 relative to the number of (meth)acryloyl groups in one molecule of (a2), and the number of carboxyl groups is not more than 0.5 relative to the number of (meth)acryloyl groups in one molecule of (a3), and
   the polyfunctional (meth)acrylate monomer comprising hydroxyl groups (a2) and the polyfunctional (meth)acrylate monomer comprising carboxyl groups (a3) comprise both of methacryloyl groups and acryloyl groups in one molecule.

2. The dental curable composition according to claim 1, wherein viscosities of both of the polyfunctional (meth)acrylate monomer comprising hydroxyl groups (a2) and the polyfunctional (meth)acrylate monomer comprising carboxyl groups (a3) are from 10 to 1,000 mPa·s (25° C.).

* * * * *